United States Patent
Hoebel

(12) 
(10) Patent No.: US 8,917,273 B2
(45) Date of Patent: Dec. 23, 2014

(54) METHOD AND DEVICE FOR PROVIDING A BIO-FEEDBACK ON A MUSCLE TRAINER

(75) Inventor: Otto Hoebel, Hochdorf (DE)

(73) Assignee: medica-Medizintechnik GmbH, Hochdorf (DE)

( * ) Notice: Subject to any disclaimer, the term of this patent is extended or adjusted under 35 U.S.C. 154(b) by 535 days.

(21) Appl. No.: 12/680,416

(22) PCT Filed: Aug. 23, 2008

(86) PCT No.: PCT/DE2008/001399
§ 371 (c)(1), (2), (4) Date: Mar. 26, 2010

(87) PCT Pub. No.: WO2009/039809
PCT Pub. Date: Apr. 2, 2009

(65) Prior Publication Data
US 2010/0302250 A1   Dec. 2, 2010

(30) Foreign Application Priority Data
Sep. 27, 2007  (DE) .......................... 10 2007 046 587

(51) Int. Cl.
G06T 11/20    (2006.01)
G09G 5/22    (2006.01)
A63B 71/06    (2006.01)
A63B 22/06    (2006.01)
A63B 22/00    (2006.01)

(52) U.S. Cl.
CPC ..... *A63B 71/0622* (2013.01); *A63B 2071/0652* (2013.01); *A63B 22/0605* (2013.01); *A63B 2022/0005* (2013.01); *A63B 2071/0638* (2013.01); *A63B 2220/54* (2013.01); *A63B 22/0007* (2013.01)
USPC ........................................ 345/440; 345/440.2

(58) Field of Classification Search
CPC ......... G06F 3/00; G06F 12/00; G06F 3/0227; G06T 13/00; A63B 2022/0005; A63B 2701/0638; A63B 2071/0652; A63B 2220/54; A63B 22/0007; A63B 22/0605; A63B 71/0622
See application file for complete search history.

(56) References Cited

U.S. PATENT DOCUMENTS 4,742,832 A * 5/1988 Kauffmann et al. .......... 600/587
4,944,288 A * 7/1990 Rawcliffe ........................ 601/33
(Continued)

FOREIGN PATENT DOCUMENTS

AU    2005100628    9/2005
DE    4413652 A1    10/1995
(Continued)

OTHER PUBLICATIONS

English Translation document of DE20210349 by Medica-Medizintechnik GMBH, Publication date: Jul. 3, 2002.*
(Continued)

*Primary Examiner* — Kee M Tung
*Assistant Examiner* — Sing-Wai Wu
(74) *Attorney, Agent, or Firm* — Muncy, Geissler, Olds & Lowe, P.C.

(57) ABSTRACT

In a method for controlling a display device on a muscle trainer equipped with at least one force sensor for sensing a person's periodic or sustained muscular force, in which display device a currently applied muscular force is depicted in relation to a target muscular force or to a maximum muscular force, and the display device is controlled such that a force queried by the patient is always depicted in a predefined target area of a panel in the display device, a multifunctional performance profile of a trainee is achieved in a clear and rapidly recognized manner in that the target muscular force is depicted by a first panel of predefined area and the currently applied muscular force is depicted by a second, variable panel positioned within the first panel, and the area of said second panel is caused to change according to a specific relationship to the currently applied muscular force.

47 Claims, 5 Drawing Sheets

(56) References Cited

U.S. PATENT DOCUMENTS

| | | | | |
|---|---|---|---|---|
| 5,382,208 | A | * | 1/1995 | Hu .................................. 482/63 |
| 5,409,435 | A | * | 4/1995 | Daniels ............................ 482/5 |
| 5,435,583 | A | * | 7/1995 | Foster, Jr. ....................... 280/237 |
| 5,527,239 | A | | 6/1996 | Abbondanza |
| 5,591,104 | A | * | 1/1997 | Andrus et al. .................... 482/7 |
| 5,769,755 | A | | 6/1998 | Henry et al. |
| 5,908,997 | A | * | 6/1999 | Arnold et al. ................... 84/615 |
| 6,155,993 | A | * | 12/2000 | Scott .............................. 600/595 |
| 2007/0137307 | A1 | * | 6/2007 | Gruben et al. ................... 73/774 |

FOREIGN PATENT DOCUMENTS

| | | |
|---|---|---|
| DE | 20210349 U1 | 10/2002 |
| DE | 202005013897 U1 | 11/2005 |
| WO | 01/95980 A2 | 12/2001 |

OTHER PUBLICATIONS

International Search Report for PCT/DE2008/001399, dated Jan. 13, 2009.

* cited by examiner

METHOD AND DEVICE FOR PROVIDING A BIO-FEEDBACK ON A MUSCLE TRAINER

BACKGROUND

The invention relates to a method for controlling a display device on a muscle trainer equipped with at least one force sensor for sensing a person's periodic or sustained muscular force, in which display device a currently applied muscular force is depicted in relation to a target muscular force or to a maximum muscular force, and the display device is controlled such that a force queried by the patient is always depicted in a predefined target area of a panel in the display device.

The invention also relates to a device for carrying out the above method.

SUMMARY

Methods and devices of the type mentioned above are used in the prior art to depict the muscular force applied by a trainee using the training apparatus and to provide an optical feedback on the force applied. However, the disadvantage of the known devices is that they are badly arranged and only poorly suitable for depicting a multifunctional force profile recognizable at a glance. A multifunctional force profile can include, for example, a force momentarily applied, as one entity, and the average constancy of a force applied over a predefined period of time, as another. In the case of training involving two force sensors respectively assigned to arm and leg activities, the uniformity of a force applied by the arms or legs can also be included in a multifunctional force profile.

It is therefore an object of the invention to provide a method and device by means of which a multifunctional force profile of a person undergoing training can be depicted in a clear and readily recognizable manner.

For a method of the type mentioned above, this object is achieved in that the target muscular force is depicted by a first panel of predefined area, and the currently applied muscular force is depicted by a second, variable panel which is positioned within the first panel, and which is caused to change its area according to a specific relationship to the currently applied muscular force.

For the device of the invention, the above object is achieved by corresponding features of the device.

Preferred embodiments of the invention are the subject matter of the dependent claims.

In the method of the invention, the combination of features according to which the target muscular force is depicted by a first panel of predefined area, and the currently applied muscular force is depicted by a second, variable panel which is positioned within the first panel and which is caused to change its area according to a predefined relationship to the currently applied muscular force, makes it possible to control a display device coupled to a training apparatus such that the varying muscular force as required over time during training sessions and the varying force applied to the training apparatus is depicted in a time-variable standard range in such a way that a patient applies the time-variable muscular force actually demanded from him over time to the apparatus taking solely into account the predefined time-variable standard range.

According to a first preferred embodiment of the method of the invention, each change in the area of the second panel is linearly proportional to the currently applied muscular force. Alternatively, each change in the area of the second panel can be quadratically proportional to the currently applied muscular force. Depending on the application, the area of the second panel can increase or decrease proportionally to the currently applied muscular force.

According to an important preferred embodiment of the method of the invention, the area of the second panel is equal to the statistical deviation, referred to as variance, from a time-averaged currently applied muscular force.

According to another important preferred embodiment of the method of the invention, when there is an increase in the currently applied muscular force to the maximum muscular force, the first panel is completely covered by the second, variable panel. The first panel preferably has a coloration which differs from that of the second, variable panel.

For example, the first panel can be of a rectangular shape and the second, variable panel can be positioned at the center of the first panel and can likewise have a rectangular shape. According to another example, the first panel can be of a circular shape and the second, variable panel can be positioned at the center of the first panel and can likewise be of circular shape.

Furthermore, the first panel can be divided into one or more distinguishable sectors, of which each depicts a predefined standard range.

In the device of the invention, the force sensor is preferably, but not necessarily, formed by a crank that can be actuated manually or by foot pressure.

In the device of the invention, the target muscular force or the maximum muscular force can be depicted by the height or the width of a first panel, and the currently applied muscular force can be depicted by a second panel positioned within the first panel, which second panel can be caused to move in the vertical direction or the horizontal direction of the first panel according to a specific relationship to the currently applied muscular force.

According to another preferred embodiment of the method of the invention, the said movement of the second panel in the vertical direction or in the horizontal direction of the first panel can be linearly proportional to the currently applied muscular force. In one possible embodiment, when there is an increase in the currently applied muscular force from a minimum muscular force to the maximum muscular force, the second panel can be caused to move from a first border region of the first panel, in the vertical direction or in the horizontal direction of the first panel, toward a second border region of the first panel opposing the first border region thereof.

In general, the first panel preferably has a coloration which differs from that of the second panel.

According to another important preferred embodiment of the method of the invention, the force sensor is formed by a crank that can be actuated manually or by foot pressure and is provided with an angle-measuring sensor which senses an angular position, and a third, movable panel, also positioned within the first panel, is caused to move, depending on the angular position of the crank, in a direction extending at right angles to the second panel.

The third panel can be controlled in such a way, for example, that when the crank is actuated evenly, the third panel is moved at a constant speed between two opposing assigned border regions. Alternatively, the third panel can be controlled such that, when the crank is actuated evenly, the third panel is moved between two opposing assigned border regions with a speed profile corresponding to a harmonic oscillation.

In both cases, the third panel can be adapted to reciprocate unidirectionally or bidirectionally.

Resistance to the muscular force being applied by a trainee can be constant over time, or alternatively, be proportional to, but acting contrary to, the muscular force applied. A time-variable standard for a time-variable muscular force to be applied to the muscle trainer is preferably, but not necessarily, provided by means of speeds that vary over time during muscle training sessions.

The preferred embodiments of the device of the invention correspond, in terms of their features, to the preferred embodiments of the method of the invention.

BRIEF DESCRIPTION OF THE DRAWINGS

The method of the invention is described below with reference to a preferred embodiment of the device of the invention illustrated in the figures of the drawings, in which.

DETAILED DESCRIPTION

Figure 3:
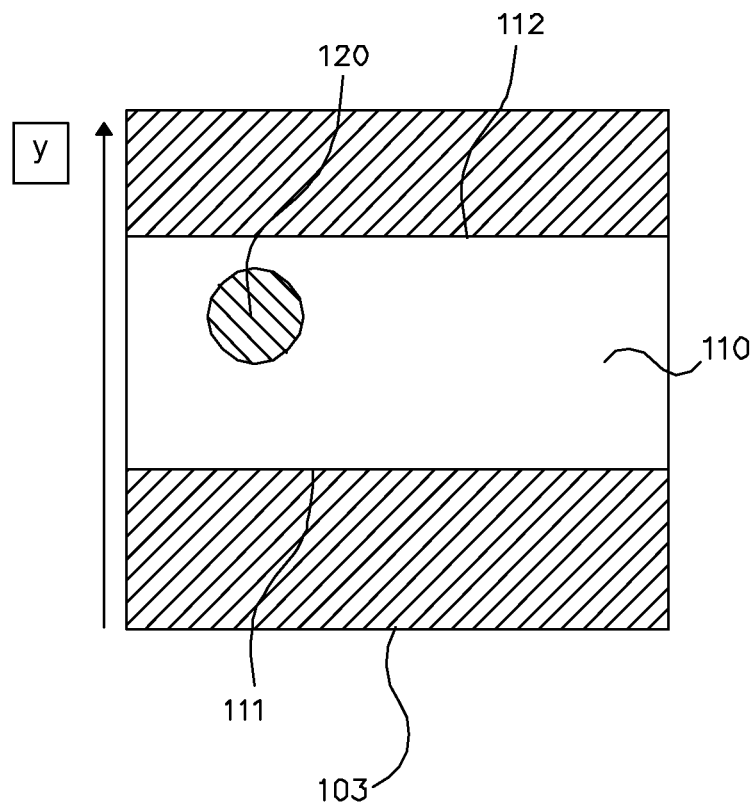
FIG. 3 is a front view of a first preferred embodiment of the display device of the invention according to a second aspect.
Figure 4:
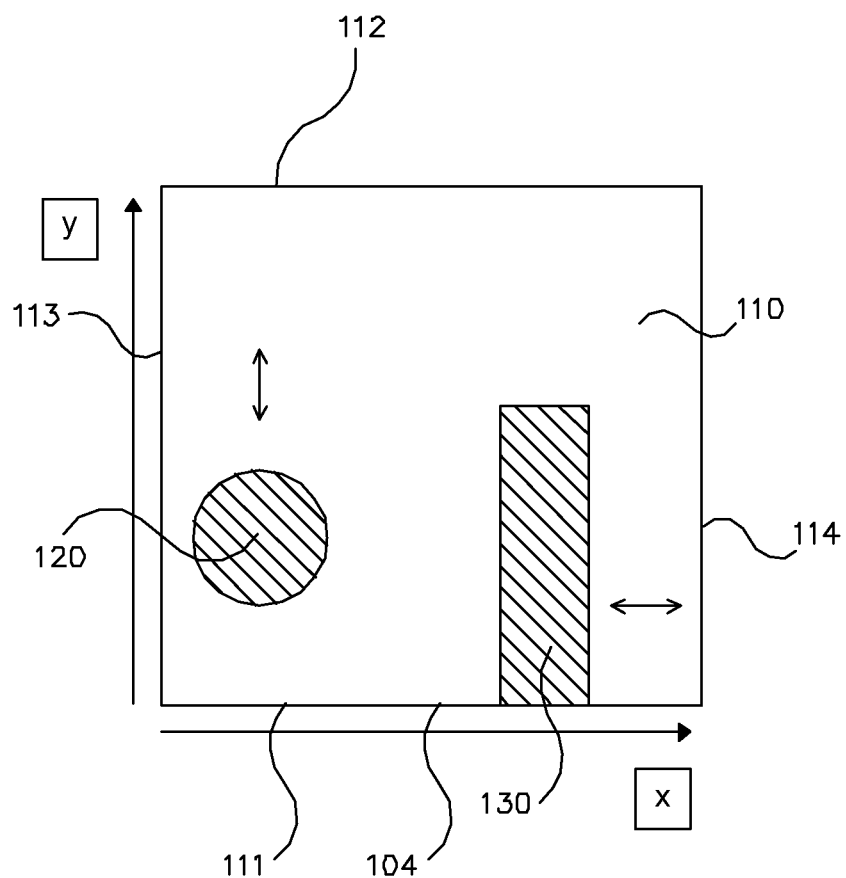
FIG. 4 is a front view of a second preferred embodiment of the display device of the invention according to a second aspect.
Figure 5:
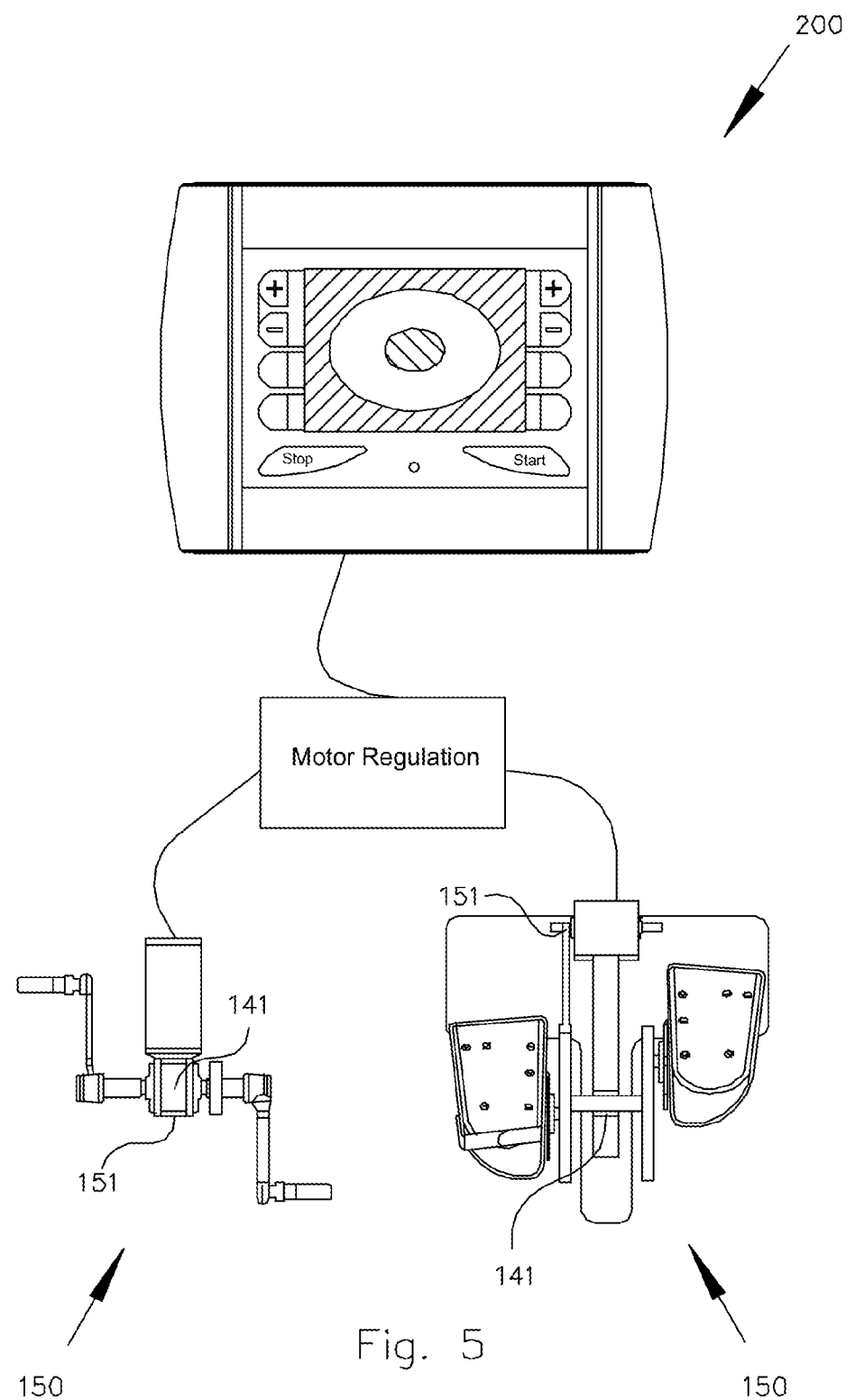
FIG. 5 is a diagrammatic illustration of the device of the invention.

The device 200 of the invention diagrammatically illustrated in FIG. 5 is designed for controlling display devices 101, 103, 104, shown in FIGS. 1 to 4 as possible embodiments, of a muscle trainer equipped with a force sensor 150 for sensing a person's periodic or sustained muscular force.

The device 200 is set up such that a resistance to the muscular force being applied by a trainee is proportional to, but acts contrary to, the muscular force applied. A time-variable default standard for a time-variable muscular force applied to the muscle trainer is provided by means of operational speeds varying over time during muscle training sessions.

In the display device 101, 103, 104, a currently applied muscular force can be depicted in relation to a target muscular force or a maximum muscular force. The display device 101, 103, 104 is controlled such that a force queried by the patient is always depicted by a predefined target region of a panel in the display device 101, 103, 104.

Figure 1:
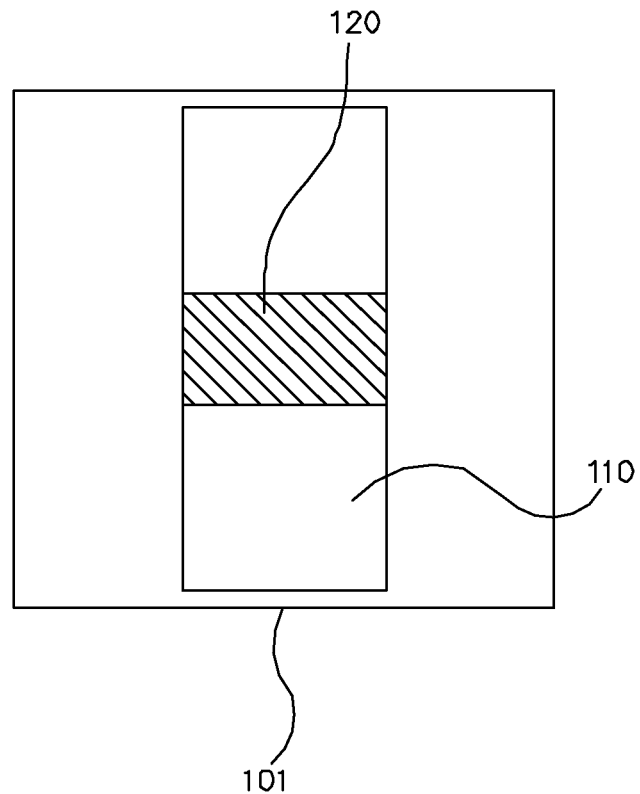
FIG. 1 is the front view of a first preferred embodiment of the display device of the invention according to a first aspect.
Figure 2:
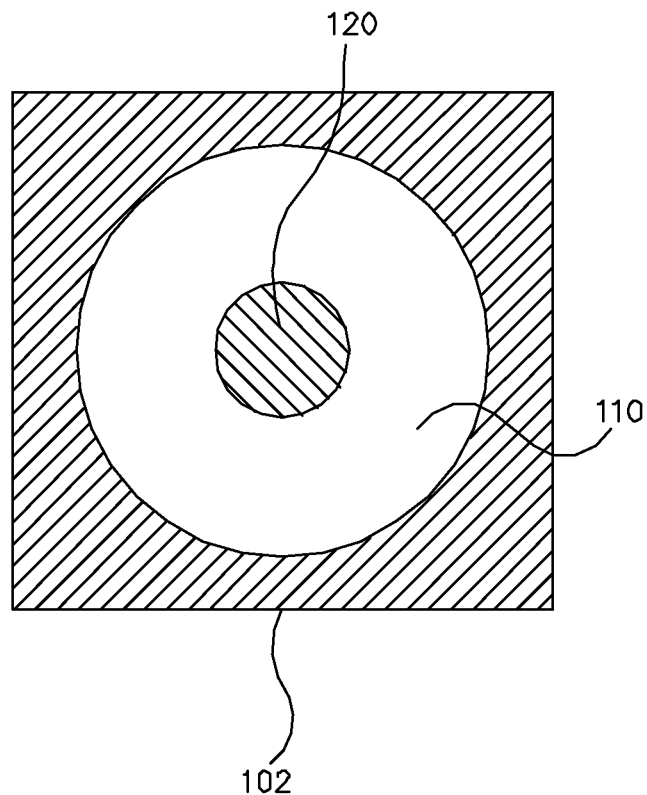
FIG. 2 is a front view of a second preferred embodiment of the display device of the invention according to a first aspect.

In the embodiments shown in FIGS. 1 and 2, the target muscular force is depicted by a first panel 110 of predefined area, and the currently applied muscular force is depicted by a second, variable panel 120 which is positioned within the first panel 110 and which is caused to change its area according to a specific relationship to the currently applied muscular force.

In the embodiment shown in FIG. 1, the increase in area of the second panel 120 is linearly proportional to the currently applied muscular force. The first panel of predefined fixed area has a rectangular shape and the second, variable panel 120 is positioned at the center of the first panel 110 and likewise has a rectangular shape.

In the embodiment shown in FIG. 2, the increase in the area of the second panel is quadratically proportional to the currently applied muscular force. The first panel 110 of predefined, fixed area has a circular shape and the second, variable panel 120 is positioned at the center of the first panel 110 and likewise has a circular shape.

In both cases, the area of the second panel 120 is equal to the statistical deviation, referred to as variance, from a time-averaged currently applied muscular force.

When there is an increase in the currently applied muscular force to the maximum muscular force, the first panel 110 is completely covered by the second, variable panel 120. The first panel 110 preferably has a coloration that differs from that of the second, variable panel 120.

The force sensor 150 is formed by a crank 151 that can be actuated manually or by foot pressure.

The display device 103, 104 of the invention, shown in FIGS. 3 and 4, for a therapeutic training apparatus likewise comprises two force sensors 150 for sensing a periodic muscular force applied, in this case to a foot pedal, by a person rotating the foot pedal. The device 200 of the invention comprises a display device 103, on which a currently applied muscular force can be depicted in relation to a target muscular force or a maximum muscular force, the target muscular force or the maximum muscular force being depicted by the height or width of a first panel 110 of predefined fixed size, and the currently applied muscular force being depicted by a second panel 120 positioned within the first panel 110, which second panel can be shifted in the vertical direction y or in the horizontal direction x of the first panel 110 according to a specific relationship to the currently applied muscular force.

The movement of the second panel 120 in the vertical direction y or in the horizontal direction x of the first panel 110 is linearly proportional to the currently applied muscular force. When there is an increase in the applied muscular force from a minimum muscular force to the maximum muscular force, the second panel 120 can be caused to move from a first border region 111 of the first panel 110 in the vertical direction y of the first panel 110 toward a second border region 112 of the first panel 110 opposing the first border region 111. The first panel 110 has a coloration that differs from that of the second panel 120.

The force sensor 150 is formed by a crank 151 that can be actuated manually and is provided with an angle-measuring sensor 141 which senses an angular position. Within the first panel 110, a third, movable panel 130 is also provided which can be caused to move in accordance with the angular position of the crank arm 151 in a direction extending at right angles to the second panel 120, that is to say, in the horizontal direction x of the first panel 110.

When the crank 151 is actuated evenly, the third panel 130 can be caused to move at a constant speed unidirectionally from the left to the right between two opposing assigned border regions 113, 114.

The exemplary embodiments of the invention described above are intended merely to provide a better understanding of the teaching of the invention defined in the claims, which teaching is not, as such, restricted to said exemplary embodiments.

The invention claimed is:

1. A method for controlling a display device of a muscle trainer equipped with at least one force sensor for sensing a person's periodic or sustained muscular force, and comprising:

depicting, in the display device, a currently applied muscular force is depicted in relation to a target muscular force; and controlling the display device is controlled such that a force queried by the patient is always depicted in a specific target region of a panel in the display device, wherein:

the target muscular force is depicted by a first panel of predefined area representing the target muscular force, and the currently applied muscular force is depicted by a second, variable panel positioned within the first panel, the area of said second panel is caused to change according to a specific relationship to the currently applied muscular force, and the target muscular force is caused to change in response to time-variable default requirements for a muscular force to be applied to the muscle trainer, such that the area of said second panel is caused to change within the first panel based on the changing of the target muscular force.

2. The method as defined in claim 1, wherein the change in the area of said second panel is linearly proportional to the currently applied muscular force.

3. The method as defined in claim 1, wherein the change in the area of said second panel is quadratically proportional to the currently applied muscular force.

4. The method as defined in claim 1, wherein the area of said second panel increases proportionally to the currently applied muscular force.

5. The method as defined in claim 1, wherein the area of said second panel decreases proportionally to the currently applied muscular force.

6. The method as defined in claim 1, wherein the area of said second panel is equal to the statistical deviation, known as variance, of a time-averaged currently applied muscular force.

7. The method as defined in claim 1, wherein when the currently applied muscular force increases to the target muscular force, the first panel of predefined fixed area is completely covered by said second, variable panel.

8. The method as defined in claim 1, wherein said first panel of predefined fixed area has a coloration that differs from that of said second, variable panel.

9. The method as defined in claim 1, wherein said first panel of predefined fixed area is rectangular in shape and said second, variable panel is positioned at the center of said first panel and is likewise rectangular in shape.

10. The method as defined in claim 1, wherein said first panel of predefined fixed area is circular in shape and said second, variable panel is positioned at the center of said first panel and is likewise circular in shape.

11. The method as defined in claim 1, wherein said force sensor is formed by a crank to be actuated manually or by foot pressure.

12. The method as defined in claim 1, wherein the target muscular force is depicted by the height or width of the first panel of predefined fixed area and the currently applied muscular force is depicted by the second panel which is positioned within said first panel and which is caused to move according to a specific relationship to the currently applied muscular force in the vertical direction or in the horizontal direction of said first panel.

13. The method as defined in claim 12, wherein the movement of said second panel in the vertical direction (y) or in the horizontal direction (x) of said first panel is linearly proportional to the currently applied muscular force.

14. The method as defined in claim 12, wherein when the currently applied muscular force increases from a minimum muscular force to the target muscular force, the second panel is caused to move from a first border region of said first panel in the vertical direction (y) or in the horizontal direction (x) of said first panel toward a second border region opposed to said first border region of said first panel.

15. The method as defined in claim 12, wherein said first panel of predefined fixed area has a coloration that differs from that of said second panel.

16. The method as defined in claim 12, wherein said first panel is divided into one or more distinguishable sectors, of which each sector represents a predefined standard range.

17. The method as defined in claim 12, wherein said force sensor is formed by a crank adapted to be actuated manually or by foot pressure and provided with an angle-measuring sensor adapted to sense an angular position, and within said first panel there is provided a third, displaceable panel which is caused to move in a direction at right angles to said second panel through a distance depending on the angular position of said crank.

18. The method as defined in claim 17, wherein when said crank is actuated evenly, said third panel is caused to move at a constant speed between two opposing assigned border regions.

19. The method as defined in claim 17, wherein when the crank is actuated evenly, said third panel is caused to move between two opposing assigned border regions with a speed profile corresponding to a harmonic oscillation.

20. The method as defined in claim 18, wherein said third panel is caused to move unidirectionally.

21. The method as defined in claim 18, wherein said third panel is caused to reciprocate bidirectionally.

22. The method as defined in claim 1, wherein a resistance counteracting the muscular force being applied by a trainee is constant over time.

23. The method as defined in claim 1, wherein a resistance counteracting the muscular force being applied by a trainee is proportional to, but acts contrary to, the muscular force applied.

24. The method as defined in claim 1, wherein the time-variable default requirements for a muscular force to be applied to the muscle trainer and changing over time are provided by means of operational speeds varying over time during muscle training sessions.

25. The method as defined in claim 1, wherein the currently applied muscular force is depicted in total by the second, variable panel as a single area caused to change in proportion to the currently applied muscular force.

26. A method for controlling a display device of a muscle trainer equipped with at least one force sensor for sensing a person's periodic or sustained muscular force, comprising:

displaying a target muscular force in a first region of a first panel, the first region having a fixed size representing the target muscular force;

changing the target muscular force in response to time-variable default requirements for a muscular force to be applied to the muscle trainer; and displaying a currently applied muscular force in a second region of the first panel overlapping the first region, the second region having a variable size or position within the first panel representing the currently applied muscular force, the size or position of the second region changing within the first panel based on the currently applied muscular force, and the size or position of the second region changing within the first panel based on the changing of the target muscular force.

27. A device for controlling a display device of a muscle trainer equipped with at least one force sensor for sensing a person's periodic or sustained muscular force, comprising:

a display controller configured to depict, in the display device a currently applied muscular force in relation to a target muscular force and to control the display device such that a force queried by the patient is depicted in a specific target region in a panel of said display device, wherein the target muscular force is depicted by a first panel of predefined area representing the target muscular force and the currently applied muscular force is depicted by a second, variable panel positioned within said first panel, the area of said second panel is caused to change according to a specific relationship to the currently applied muscular force, wherein the target muscular force is caused to change in response to time-variable default requirements for a muscular force to be applied to the muscle trainer, such that the area of said second panel is caused to change within the first panel based on the changing of the target muscular force.

28. The device as defined in claim 27, wherein the change in area of said second panel is linearly proportional to the currently applied muscular force.

29. The device as defined in claim 27, wherein the change in area of said second panel is quadratically proportional to the currently applied muscular force.

30. The device as defined in any one of claim 27, wherein the area of said second panel increases proportionally to the currently applied muscular force.

31. The device as defined in claim 27, wherein the area of said second panel decreases proportionally to the currently applied muscular force.

32. The device as defined in claim 27, wherein the area of said second panel is equal to the statistical deviation, known as variance, of a time-averaged currently applied muscular force.

33. The device as defined in claim 27, wherein when there is an increase in the currently applied muscular force to the target muscular force, the first panel of predefined fixed area is completely covered by said second, variable panel.

34. The device as defined in claim 27, wherein said first panel of predefined fixed area has a coloration that differs from that of said second, variable panel.

35. The device as defined in claim 27, wherein said first panel of predefined fixed area is rectangular in shape and said second, variable panel is positioned at the center of said first panel and is likewise rectangular in shape.

36. The device as defined in claim 27, wherein said first panel of a predefined fixed area is circular in shape and said second, variable panel is positioned at the center of said first panel and is likewise circular in shape.

37. The device as defined in claim 27, wherein said force sensor is formed by a crank to be actuated manually or by foot pressure.

38. The device as defined in claim 27, wherein the target muscular force is depicted by the height or width of a first panel of predefined fixed area and the currently applied muscular force is depicted by a second panel which is positioned within said first panel and which is caused to move in a specific relationship to the currently applied muscular force in the vertical direction (y) or in the horizontal direction (x) of said first panel.

39. The device as defined in claim 38, wherein the movement of said second panel in the vertical direction (y) or in the horizontal direction (x) of said first panel is linearly proportional to the currently applied muscular force.

40. The device as defined in claim 38, wherein when there is an increase in the currently applied muscular force from a minimum muscular force to the target muscular force, the second panel is caused to move from a first border region of said first panel in the vertical direction (y) or in the horizontal direction (x) of said first panel toward a second border region of said first panel which is opposed to said first border region.

41. The device as defined in claim 38, wherein said first panel of predefined fixed area has a coloration that differs from that of said second panel.

42. The device as defined in claim 38, wherein said force sensor is formed by a crank which is to be actuated manually or by foot pressure and is provided with an angle-measuring sensor for sensing an angular position, and within said first panel there is provided a third, displaceable panel which is caused to move in a direction at right angles to said second panel depending on the angular position of said crank.

43. The device as defined in claim 42, wherein when the crank is actuated evenly, said third panel is caused to move at a constant speed between two opposing assigned border regions.

44. The device as defined in claim 42, wherein when the crank is actuated evenly, said third panel is caused to move between two opposing assigned border regions with a speed profile corresponding to a harmonic oscillation.

45. The device as defined in claim 42, wherein said third panel is caused to move unidirectionally.

46. The device as defined in claim 42, wherein said third panel is caused to reciprocate bidirectionally.

47. The device as defined in claim 27, wherein said first panel is divided into one or more distinguishable sectors, of which each sector represents a predefined standard range.

* * * * *